United States Patent [19]

Tsuji et al.

[11] 4,004,693
[45] Jan. 25, 1977

[54] APPARATUS FOR INSPECTING THE DISPOSITION OF STEEL PLY CORDS IN PNEUMATIC TIRES

[75] Inventors: Naotaka Tsuji; Koji Yamada, both of Kodaira, Japan

[73] Assignee: Bridgestone Tire Company Limited, Kyoba, Japan

[22] Filed: Apr. 23, 1975

[21] Appl. No.: 570,796

[30] Foreign Application Priority Data

May 9, 1974 Japan .............................. 49-51666

[52] U.S. Cl. ............................... 209/81 R; 73/146; 209/74 R; 209/75; 209/82; 324/40
[51] Int. Cl.² ........................ B07C 5/04; B07C 5/08
[58] Field of Search ............. 209/73, 74, 75, 81 R, 209/81 A, 82, 88 R, 111.5, 111.8; 324/3, 40; 73/146; 250/358 T

[56] References Cited

UNITED STATES PATENTS

| 2,519,367 | 8/1950 | Gunn et al. | 324/40 |
|---|---|---|---|
| 3,089,576 | 5/1963 | Sauer et al. | 198/29 |
| 3,249,869 | 5/1966 | Meyer et al. | 324/40 |
| 3,549,985 | 12/1970 | Pewland | 324/3 |
| 3,631,716 | 1/1972 | Monajjem | 73/146 |
| 3,852,600 | 12/1975 | Faulkner et al. | 250/358 T |
| 3,883,744 | 5/1975 | Steffel | 250/358 T X |
| 3,895,716 | 7/1975 | Ugo | 209/74 M |

*Primary Examiner*—Robert B. Reeves
*Assistant Examiner*—Joseph J. Rolla

[57] ABSTRACT

An apparatus for inspecting the disposition of reinforcing steel ply cords in pneumatic tires. The apparatus can inspect a desired number of tires successively in a full-automatic fashion, classifying the inspected tires at the discharging end of the apparatus according to the results of the inspection. The tire inspecting apparatus comprises in combination a tire feeding mechanism for feeding tires one by one toward a predetermined position on the apparatus, a tire retaining mechanism for rotatably retaining a tire in an inspecting position, a rotational driving mechanism mechanically connected to the tire retaining mechanism, a cord disposition detecting unit having electric detectors and mounted movably on a carriage for moving the detectors toward and away from positions facing opposite side wall portions of the tire, an electric control circuit connected to the detectors of the cord disposition detecting mechanism to produce a disqualifying signal upon detection of an irregularity in the disposition of the steel ply cords in the tire, and a classifying mechanism for distinguishing a disqualified tire from qualified ones.

9 Claims, 11 Drawing Figures

APPARATUS FOR INSPECTING THE DISPOSITION OF STEEL PLY CORDS IN PNEUMATIC TIRES

This invention relates to an apparatus for inspecting pneumatic tires reinforcing steel ply cords, and more particularly to an apparatus for inspecting the disposition or distribution of radial steel ply cords in pneumatic tires.

In the production of pneumatic vehicle tires which have radial reinforcing steel ply cords embedded for reinforcing purposes, there sometimes occur irregularities in the disposition of the steel ply cords which are anchored radially in the tire for reinforcing purposes, for example, abnormally narrow or wide spacings between certain cords or of adjacent cords. Such irregularities in the disposition of the cords can result in dangerous accidents since the tires which have non-uniformly distributed cords will easily rupture when mounted on vehicles. For this reason, it is a mandatory requisite for the tire manufacturers to carry out strict inspections in this regard.

The inspections of the steel ply cord disposition or distribution usually depends on judgements of experienced inspectors who check the products mainly on the basis of appearance and feeling by fingers, resulting in unacceptably low accuracy.

It is also known to inspect the tires by X-ray photographs or by a TV monitor. However, these methods are time-consuming and require a large investment for the inspection facilities. Especially, the method using the TV monitoring is undesirable in that it causes considerable fatigue to the inspector.

With the foregoing in view, the present invention has as its object the provision of an apparatus which is capable of automatically inspecting the disposition of steel ply cords of pneumatic vehicle tires without relying on the personal perceptions of the inspector.

It is another object of the present invention to provide an apparatus of the above type, which is capable of inspecting a desired number of tires successively and classifying the tires according to the results of the inspection.

It is a further object of the invention to provide an apparatus of the above type, which is simple in construction and which can be fabricated at a low cost.

These objects can be achieved by an apparatus which comprises: a tire feeding mechanism for feeding tires one by one toward a predetermined position on said apparatus; a tire retaining mechanism having a rim member split into upper and lower halves for rotatably retaining a tire in an inspecting position; a rotational driving mechanism mechanically connected to the rim member for rotatingly driving same; cord disposition detecting means having electric detectors and mounted movably on a carriage on the apparatus for moving the electric detecting means toward and away from inspecting positions facing opposite side wall portions of said tire; an electric control circuit connected to said electric detectors and adapted to produce a disqualifying signal upon detection of an irregularity in the disposition of the steel ply cords in the tire; and classifying means for distinguishing a disqualified tire from qualified ones.

The feeding mechanism may be a roller conveyer with a suitable stopper mechanism for intermittently releasing the tires one by one upon completion of the inspection of a preceding tire. This can be attained by providing a pair of arms swingably across a tire passage on the roller conveyor and connected through suitable linkages to a fluid-operated motor which is intermittently actuated to move the arms away each other to open the tire passage.

According to the invention, in order to retain the tire rotatably at the inspecting position on the apparatus, the upper half of the split rim member is securely mounted at a lower end of an upper vertical shaft which is rotatably supported on a machine frame and which is connected to an output shaft of an electric motor through a reduction gear unit. While the lower half of the split rim is securely mounted at an upper end of a lower vertical rotary shaft in axial alignment with the upper half. The lower vertical rotary shaft is driven from a fluid-operated actuator toward and away from the inspecting position together with the tire to be inspected, the lower rotary shaft having an axially extending air passage connected to a compressed air source for blowing compressed air into the tire prior to the inspecting operation.

Preferably, the tire inspecting apparatus includes a tire size detecting means which comprises, for example, an arm member securely mounted on a cam shaft and rotatingly movable toward a tread surface of a tire which has been delivered to the predetermined center position on the apparatus, a number of cam plates securely mounted on the cam shaft and having angularly displaced cam surfaces relative to the axis of the cam shaft, and a number of limit switches securely mounted on a machine frame opposingly to the respective cam plates, so that the cam plates actuate the limit switches in a number corresponding to an angle of rotational movement of the arm member to produce a signal indicative of the size of the tire. Upon receipt of the signal from the tire size detecting means, the carriage which supports the cord disposition detecting mechanism thereon is moved by a distance suitable for bringing the detectors into positions facing opposite side wall portions of the tire. In this connection, a limit mechanism is provided in the present invention to limit the movement of the carriage, including a plate member securely mounted on a carriage frame and having a number of consecutively stepped edges, and a number of limit switches securely mounted on a machine frame opposingly to the consecutively stepped edges of the plate member. The carriage may be moved toward and away from the tire in the inspecting position by means of a conventional mechanism, for example, by providing in threaded engagement with the carriage a screw rod which is rotatably mounted on a machine frame and connected at one end to a reversible electric motor through a suitable speed reduction gear unit.

According to the invention, the detectors of the cord disposition detecting mechanism each on an iron core has a primary coil which is connected to an oscillator and a secondary or differential coil which is connected to the electric control circuit through an amplifier. The primary and differential windings on the iron core is housed in a casing which is of a non-magnetic material, preferably of tetrafluoro-ethylene, and filled with a synthetic resin material. With this detector construction, a weak voltage is produced in the differential coil when the detector is passed over steel ply cords which have an irregular spacing therebetween or which are overlapped on one another. This weak voltage is fed, after suitable amplification, to the control circuit which identifies the irregularity and produces a disqualifying signal to actuate suitable marking means.

The above and other objects, features and advantages of the invention will become clear from the following description, taken in conjunction with the accompanying drawings which form part of this specification and which show by way of example one preferred embodiment of the invention.

Figure 1:
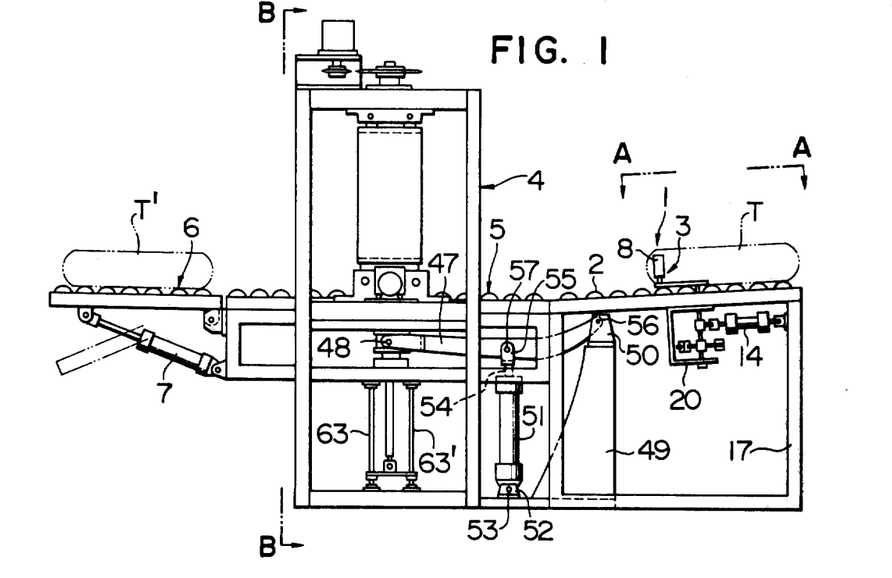
FIG. 1 is a schematic front view of a tire inspection apparatus according to the invention.

Referring now to the accompanying drawings, FIG. 1 schematically shows the general construction of a tire inspecting apparatus according to the present invention, which includes a tire feeding mechanism in the form of a roller conveyer 2 which is provided with an intermittently operative stop mechanism 3 for feeding tires one by one in a predetermined timed cycle to a predetermined position on the main body of the inspection apparatus generally indicated at 4. More particularly, the tires T are fed one by one from the conveyer 1 onto an adjoining roller conveyer 5 which transfers a received tire T to a centering mechanism (not shown) for positioning the tire T in a predetermined center position on the inspection apparatus body 4. Designated at 6 is a discharging conveyer which is mounted rockably at the discharging end of the conveyer 5 and driven from a fluid-operated piston-cylinder device 7 to assume either a horizontal position or an inclined or slanting position for sending straight forward or dropping the inspected tire according to the results of the inspection.

Figure 2:
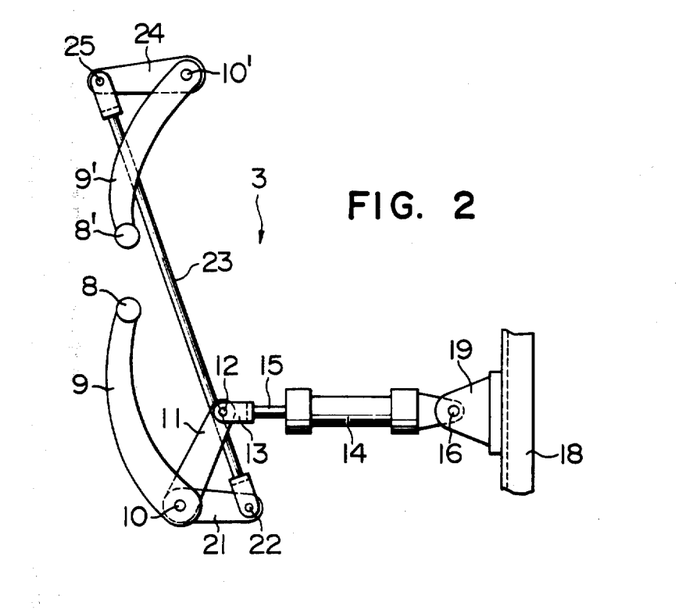
FIG. 2 is a schematic plan view of a stopper mechanism, taken on line A—A of FIG. 1.

Referring now to FIG. 2, the stopper mechanism 3 of the feeding conveyer 1 includes a pair of stopper rollers 8 and 8' at inner ends of arm members 9 and 9', the outer ends of which arm members being securely supported on shafts 10 and 10', respectively. The shaft 10 also fixedly supports thereon one end of a link member 11 which has the other end pivotally supported through a pin member 12 on a U-shaped bracket 13 which is in turn securely mounted at a fore end of a piston rod 15 of a fluid-operated piston-cylinder 14. The rear or bottom end of the fluid-operated piston-cylinder 14 is connected by a pin member 16 to a bracket 19 which is securely mounted on a beam 18 on a frame structure 17 of the feeding conveyer 1. The afore-mentioned shafts 10 and 10' are pivotally supported on a bracket 20 on the frame 17 of the conveyer 1. The reference numeral 21 denotes a link member which has one end secured to the shaft 10 and the other end pivotally connected by a pin member 22 to a U-shaped connecting piece at one end of a connecting rod member 23. The connecting rod member 23 has a similar U-shaped connecting piece at the other end for pivotally supporting one end of another link member 24 on a pin member 25, the other end of the link member 24 being fixedly supported on the afore-mentioned shaft 10'. As will be seen in FIG. 2, the link member 24 is mounted on the shaft 10' in a direction reverse to the direction in which the link member 21 is mounted on the shaft 10.

Figure 3:
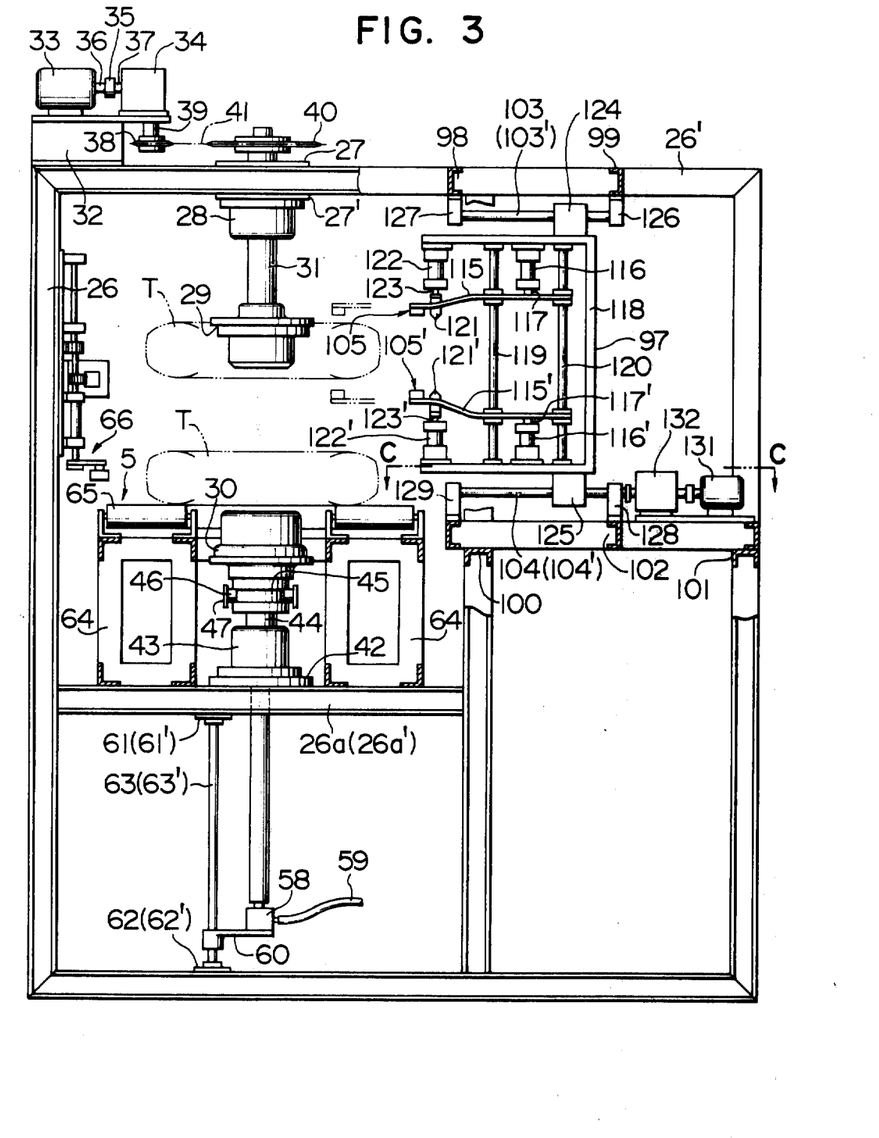
FIG. 3 is a schematic side view of the inspection apparatus, taken on line B—B of FIG. 1.

Referring to FIG. 3, the inspection apparatus has opposite side frames 26 and 26'. The frames 26 and 26' securely support thereon plate members 27 and 27' for mounting a bearing 28. Indicated at 29 and 30 are upper and lower rim halves which hold bead portions of a tire T to be inspected. The upper rim member 29 is securely mounted at the lower end of a shaft 31 which is rotatably supported in its middle portion on the afore-mentioned bearing 28. A bracket 32 is securely supported on the frame 26 for mounting thereon a brake-equipped electric motor 33 and a reduction gear unit 34. The output shaft 36 of the motor 33 is connected to an input shaft of the reduction gear unit 34 through a coupling 35. The output shaft of the reduction gear unit 34 has mounted thereon a sprocket wheel 38. A chain 41 is passed around the sprocket wheel 38 and another sprocket wheel 40 which is fixedly mounted on the upper end of the shaft 31. The lower rim member 30 is fixedly mounted at the upper end of a shaft 44 which is rotatably supported in a bearing 43. The just-mentioned bearing 43 is mounted on a plate 42 which is bridged between cross members 26a and 26a'. The lower rim member 30 has an annular groove 45 at the lower end which is integrally connected to the shaft 44. The annular groove 45 is in engagement at opposite sides with rim holders 46 which are rotatably supported on pin members 48 at a bifurcated end of a lever arm 47 which is shown particularly in FIG. 1. Provided immediately beneath the feeding conveyer 1 is a fixed frame 49 which has a bracket 50 securely mounted on its upper end. A fluid-operated piston-cylinder 51 is provided for moving the lower rim member 30 up and down. The lower end of the piston-cylinder device 51 is mounted by a pin 53 on a bracket 52 which is fixedly secured to the frame 49. The fluid-operated piston-cylinder device 51 has a U-shaped bracket 55 fixedly secured to the end of piston rod 54. The above-mentioned lever arm 47 has its rear end and center portion supported on the brackets 50 and 55 through pin members 56 and 57, respectively. The lower end of the shaft 44 is connected to a rubber hose 59 through a rotary joint 58 as shown particularly in FIG. 3. The rotary joint 58 is supported on a bracket 60 which is slidably supported on guide rod members 63 and 63' which are journalled in bearings 61, 61', 62 and 62' on the beams or cross members 26a and 26a' and the lower members of the body frames 26 and 26', respectively.

Figure 4:
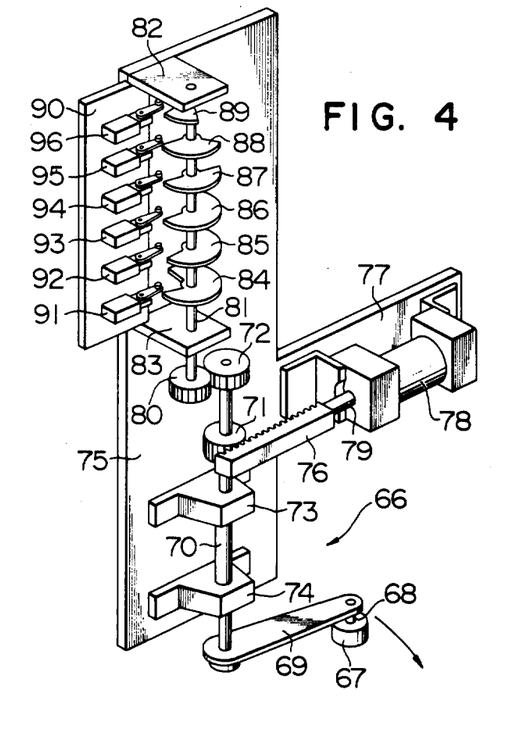
FIG. 4 is a schematic perspective view of a tire size detecting mechanism.

The lower rim member 30 is provided with an air blowing outlet (not shown) at the terminal end of an air passage (not shown) which is formed axially through the body of the shaft 44 and which communicates with an air feed device (not shown) through the rotary joint 58 and the rubber hose 59 for introducing or exhausting air into or from the tire T. The lower frames 64 of the roller conveyer 5 are supported on the beams 26a and 26a'. The roller conveyer 5 has a number of shortened rollers 65 in the middle portion to provide therebetween an opening through which the lower rim member 30 is allowed to move up and down while grippingly holding the tire T during the inspection. Indicated at 66 is a tire size detector for measuring the outer diameter of the tire T when the latter is held in a center position on the conveyer 5 by the afore-mentioned centering mechanism (not shown), the tire size detector 66 being mounted at a suitable level on the upright posts of the body frames 26 and 26'. More particularly, referring to FIG. 4, the tire size detector 26 includes a detection roller 67 which is movable for contact with the tread surface of the tire T to be inspected. The detection roller 67 is rotatably supported at one end of an arm 69 by means of a pin member 68. The other end of the arm 69 is fixedly supported at a lower end of a shaft 70 which fixedly mounts thereon a pinion gear 71 and a gear 72 at the other or upper end thereof. The shaft 70 is supported on a plate 75 by means of bearings 73 and 74. The aforementioned pinion gear 71 is in meshing engagement with a rack 76 one end of which is threadedly connected to a piston rod 79 of a fluid-operated piston-cylinder device 78 which is securely mounted on a projection or extension 77 of the plate member 75. The gear 72 at the upper end of the shaft 70 is in mesh with a gear 80 which is securely mounted at a lower end of a shaft 81, which is in turn supported on the plate member 75 by means of bearings 82 and 83. The shaft 81 securely supports thereon a number of cam plates 84 to 89 at suitable intervals along the length of the shaft 81. These cam plates 84 to 89 are formed in particular shapes such that a number of limit switches 91 to 96 which are mounted opposingly in predetermined positions on the plate 75 by means of a mounting plate 90 are actuated sequentially as the detection roller 67 is rotatingly moved into contact with the tread surface of the tire T upon actuation of the fluid-operated piston-cylinder 78. For example, if the detection roller 67 comes into contact with the tread surface of the tire T just when the gear 72 has completed a half turn, limit switches 91 to 94 are actuated due to the particular angular positions of the cam plates 84 to 87. As a result, it is known that the tire T to be inspected has an outer diameter which is represented by the limit switch 94.

Referring to FIG. 3, a radial cord distribution detecting mechanism which is generally indicated at 97 is mounted between upper beams 98 and 99 and lower beams 100 and 101, the cord distribution detecting mechanism 97 being slidingly movable along guide rods 103 and 103' which are bridged between the upper beams 98 and 99 and along guide rods 104 and 104' which are securely mounted on a table 102 on the lower beams 100 and 101. The cord distribution detecting mechanism 97 includes a pair of detectors 105 and 105' each having, as shown particularly in FIG. 7, a primary coil 108 and a secondary or differential coil 106 wound on an iron core 107. Indicated at 111 and 112 are terminals of the primary coil 108 and at 109 and 110 terminals of the differential coil 106. The primary and differential coils 108 and 106 are enclosed in a casing 113 of Teflon (a trademark of E. I. duPont de Nemours & Co. for tetrafluoroethylene) which has an inner space 114 filled with a synthetic resin material.

Figure 6:
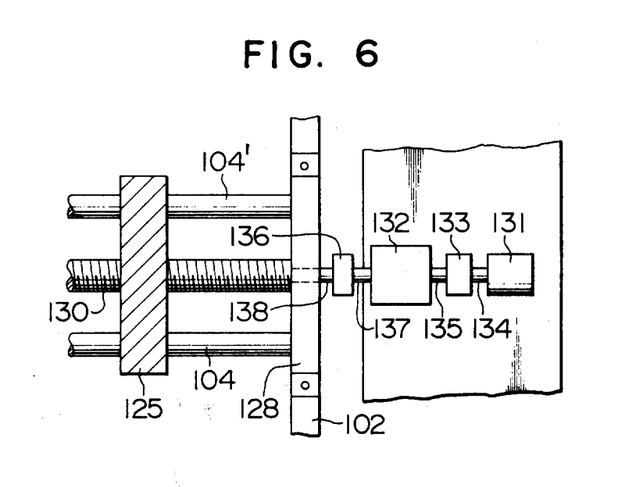
FIG. 6 is a schematic plan view of a carriage driving mechanism, taken on line C—C of FIG. 3.

In FIG. 3, the reference numeral 115 designates a support for the detector 105, which support 115 is securely connected to a piston rod 117 of a fluid-operated piston-cylinder 116 at a position between the guide rods 119 and 120. The forward end of the piston-cylinder device 116 is supported on an upper frame of a carriage 118 which is generally of a rectangular shape. The carriage 118 has two vertical guide rods 119 and 120 for the purpose of guiding the vertical movements of the detector support 115. A marking member 121 is provided in a position proximate to the detector 105, securely at the projected end of a piston rod 123 of a fluid-operated piston-cylinder 122. The piston-cylinder 122 has the forward end of the cylinder securely supported at the fore end of the upper frame of the carriage 118. The reference numeral 115' designates a support for the detector 105', which support 115' is securely connected to a piston rod 117' of a fluid-operated piston-cylinder 116' at a position between the guide rods 119 and 120. The forward end of the piston-cylinder device 116' is supported on a lower frame of a carriage 118. The vertical guide rods 110 and 120 are also adapted to guide the vertical movements of the detector support 115'. A marking member 121' is provided in a position proximate to the detector 105', securely at the projected end of a piston rod 123' of a fluid-operated piston-cylinder 122'. The piston-cylinder 122' has the forward end of the cylinder securely supported at the fore end of the upper frame of the carriage 118. The carriage 118 further has upper and lower guide followers 124 and 125 secured to the upper and lower frames thereof. The upper guide follower 124 is slidably engaged with the guide rods 103 and 103' which are supported in bearings 126 and 127. On the other hand, the lower guide follower 125 is held in sliding engagement with the guide rods 104 and 104' which are supported in bearings 128 and 129. As shown in FIG. 6, a screw rod 130 is rotatably supported in bearings 128 and 129 between the guide rods 104 and 104' to be in threaded engagement with the lower guide follower 125 of the carriage 118. In FIG. 6, the reference numeral 131 indicates a brake-equipped electric motor and 132 a reduction gear unit. The output shaft 134 of the motor 131 is connected to an input shaft 135 of the reduction gear unit 132 through a coupling 133. The output shaft 137 of the reduction gear unit 132 is connected to a driven end 138 of the screw rod 130 through a coupling 136.

Figure 5:
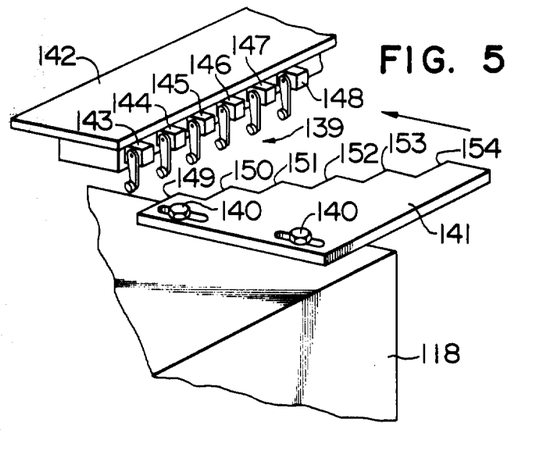
FIG. 5 is a schematic perspective view of a limit mechanism which is employed for limiting the distance of travel of a detector carriage.

Referring to FIG. 5, a limit mechanism 139 which is generally designated at 139 is mounted on the upper frame of the carriage 118 for limiting the distance of movement of the carriage 118. The limit mechanism 139 includes a cam plate 141 which is fixed on the upper frame of the carriage 118 by screws 140, and a number of limit switches 143 to 148 which are securely mounted on the body frame 26' by means of a pendent bracket 142. The cam plate 141 has stepped edge portions 149 to 154 opposed to the afore-mentioned limit switches 143 to 148 to locate the detectors 105 and 105' at inspection points on the opposite side walls of the tire T, in relation with the operation of the limit switches 91 to 96 of the tire diameter detecting mechanism 66.

Figure 7:
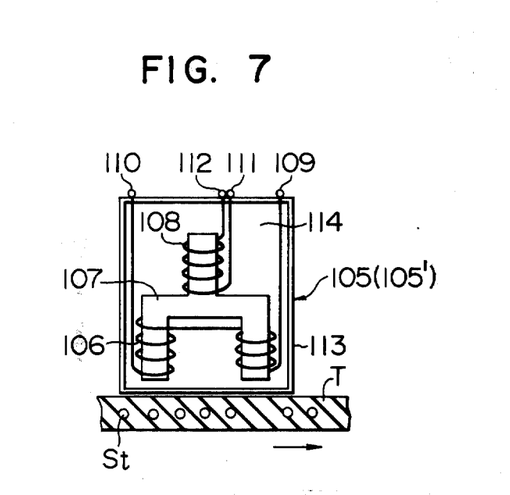
FIG. 7 is a schematic sectional view of a detector.
Figure 8:
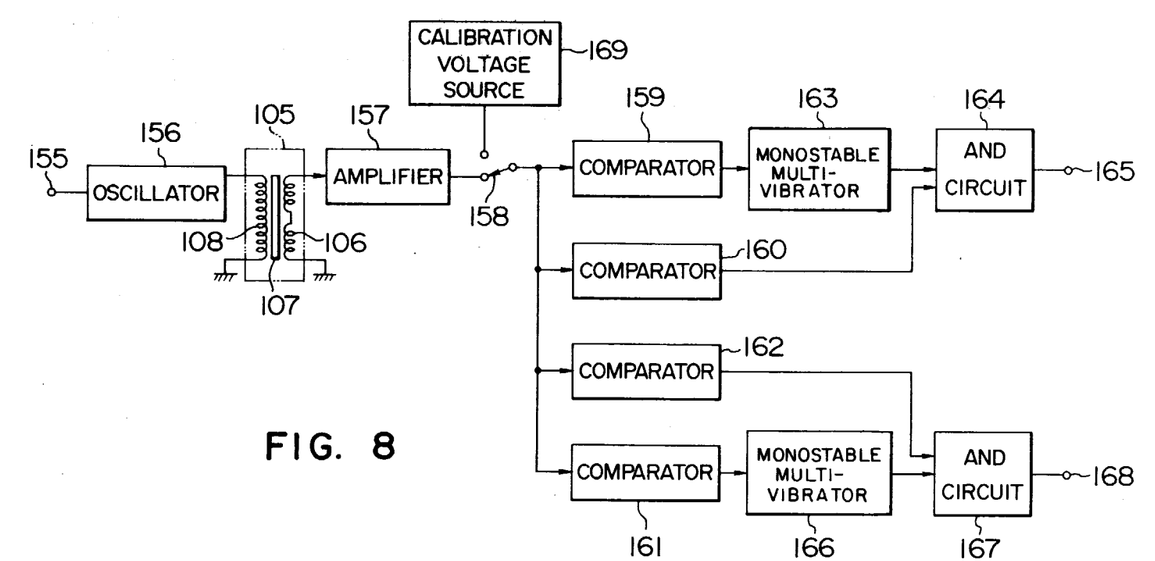
FIG. 8 is a block diagram of an electric control circuit which produces a disqualifying signal upon detection of an irregularity in the disposition of the steel ply cords.
Figure 9:
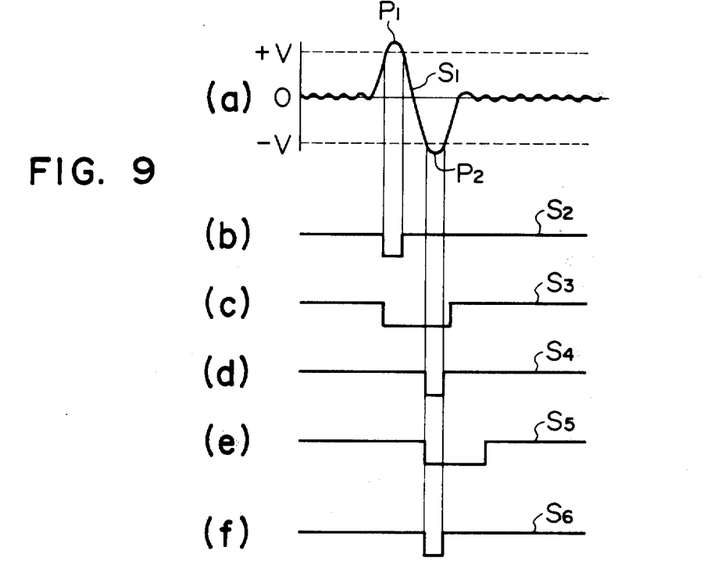
FIGS. 9 and 10 are diagrammatic views showing various signals appearing in the electric control circuit of FIG. 8.

FIG. 8 shows in a block diagram an electric control circuit of the cord distribution detecting mechanism 97 which detects irregularities in the cord distribution in the side walls of the tire T through detectors 105 and 105'. In the particular embodiment of the invention, the tire inspection apparatus is provided with a pair of detectors 105 and 105' for simultaneously detecting irregularities in the cord distribution in the opposite side walls of the tire T as shown in FIG. 3. However, FIG. 8 shows only one electric control circuit for the upper detector 105 as the other detector 105' has a control circuit of the same arrangement. The control circuit includes a power supply terminal 155 for supplying power to an oscillator 156 which generates a voltage of 5KHz to energize the primary coil 108 of the detector 105. When the detector 105 passes over steel ply cords which have an abnormally wide gap therebetween as shown in FIG. 7, a weak voltage is produced in the differential coil 106. This weak voltage is amplified in an amplifier 157 which, as a result, produces an output signal S1 in the wave form as shown at (a) of FIG. 9. This output signal S1 is fed through a change-over switch 158 to comparators 159 to 162.

Prior to the initiation of the inspecting operation, the comparators 159 to 162 are connected to a calibration voltage source 169 through the change-over switch 158 and calibrated to have a threshold voltage level V. More particularly, in the particular embodiment shown, the comparators 159 and 162 are calibrated to have a threshold voltage level of +V and produce an output signal S2 as shown at (b) of FIG. 9 when the input signal S1 at (a) of FIG. 9 exceeds the threshold voltage +V in the positive phase P1. On the other hand, the comparators 160 and 161 are calibrated to have a threshold voltage of −V and produce an output signal S4 as indicated at (d) of FIG. 9 where the input signal S1 at (a) of FIG. 9 exceeds the threshold voltage −V in the negative phase P2. The output signal S2 of the comparator 159 is fed as an input signal to a monostable multivibrator 163. The monostable multivibrator 163 retains the input signal S2 for a predetermined time period to produce an output signal S3 as at (c) of FIG. 9. The output signal S3 from the monostable multivibrator 163 is fed to an AND circuit 164 which is also fed with an output signal S4 of the comparator 160. In a similar manner, an output signal S4 of the comparator 161 is fed as an input signal to a monostable multivibrator 166, which retains the input signal S4 for a predetermined time period to produce an output signal S5 as at (e) of FIG. 9. The output signal S2 of the comparator 162 is fed to an AND circuit 167 together with the output signal S5 from the monostable multivibrator 166. Though the AND circuit 167 is fed with both the signals S2 and S5, it produces no output signal since the signals S2 and S5 do not coincide with each other as shown at (b) and (e) of FIG. 9. On the other hand, the AND circuit 164 receives the input signals S3 and S4 which coincide with each other as shown at (c) and (d) of FIG. 9, so that the AND circuit 164 produces an output signal S6 as at (f) of FIG. 9 at its output terminal 165. The output terminal 165 is connected to an auxiliary relay (not shown) and an electromagnetic valve (not shown) which is adapted to be actuated upon receipt of the signal S6 to supply a fluid pressure to the piston-cylinder 122 of FIG. 3 for putting a mark on the tire T by means of the marking member 121.

The operations of the cord distribution detector control circuit discussed in the foregoing description occur when the detector 105 passes over steel ply cords which are abnormally spaced apart from each other. In a case contrary to this, namely, in a case where the steel ply cords have an abnormally narrow spacing therebetween or where they are in an overlapped state, the control circuit operates as follows. When the detector 105 comes over a side wall portion of the tire T which contains abnormally narrowly spaced steel ply cords St, a weak voltage is produced in the differential coil 106. This weak voltage is amplified by an amplifier 157 which, as a result, produces an output signal S1' in the wave form as shown at (a) of FIG. 10. The output signal S1' is fed through a change-over switch 158 to comparators 159 to 162. The comparators 159 and 162 are calibrated to produce an output signal S4' as at (d) of FIG. 10 when the input signal S1' at (a) of FIG. 10 exceeds a threshold voltage level +V in the positive phase P1'. On the other hand, the comparators 160 and 161 are calibrated to produce an output signal S2' as at (b) of FIG. 10 when the input signal S1' at (a) of FIG. 10 exceeds a threshold voltage level of −V in the negative phase P2'.

Figure 10:
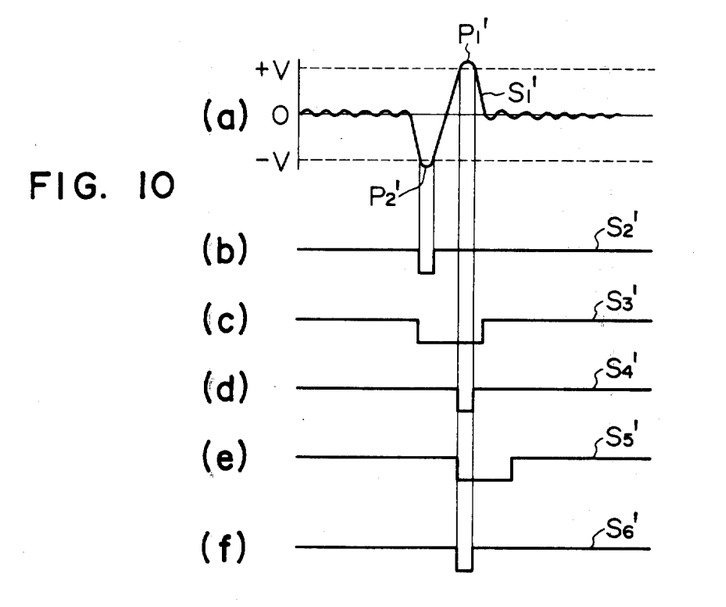

The output signal S4' from the comparator 159 is fed as an input signal to the monostable multivibrator 168, which retains the input signal S4' for a predetermined time period to produce and supply an output signal S5' as at (e) of FIG. 10 to the AND circuit 164. The output signal S2' of the comparator 160 is also fed as an input signal to the AND circuit 164. While, the output signal S2' from the comparator 161 is fed as an input signal to the monostable multivibrator 166, which retains the input signal for a predetermined time period to produce an output signal S3' as at (c) of FIG. 10. The output signal S3' from the monostable multivibrator 166 is fed to the AND circuit 167 which also receives as an input signal the output signal S4' from the comparator 162.

In this instance, the AND circuit 164 receives both of the input signals S2' and S5' but it produces no output signal since the input signals S2' do not coincide with each other as shown at (b) and (e) of FIG. 10. On the other hand, the AND circuit 167 receives the input signals S3' and S4' which coincide with each other as indicated at (c) and (d) of FIG. 10. Thus, the AND circuit 167 produces at its output terminal 168 an output signal S6' as at (f) of FIG. 10, which serves to actuate the marking mechanism in a manner similar to the output signal S6 which appears at the output terminal 165.

Figure 11:
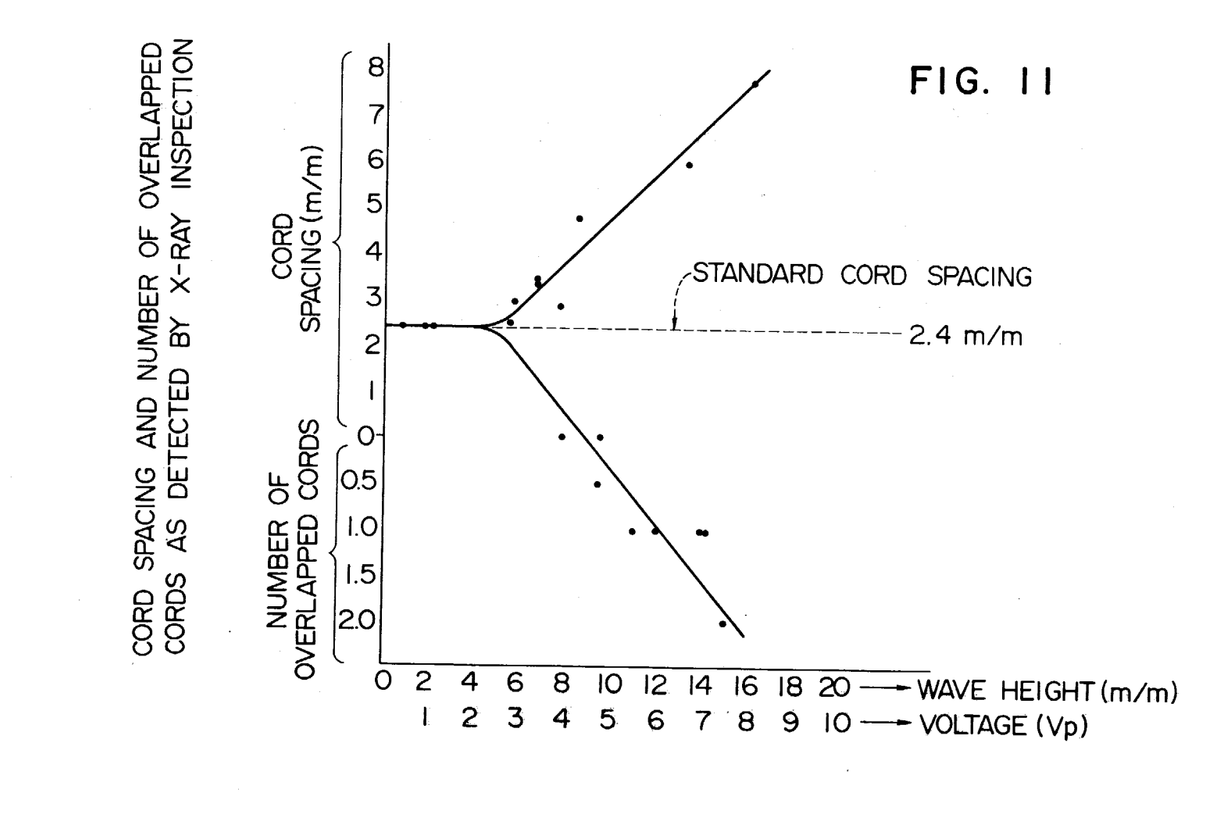
FIG. 11 is a graphic illustration showing the relation between the spacing or overlapping of the steel ply cords as detected by an X-ray inspection and the voltage as detected by the detector of the invention.

FIG. 11 is a graphic illustration showing the relations between the spacing or overlapping of the steel ply cords St as detected by X-ray inspection and a voltage Vp as detected by the detector 105 with use of a tire having a standard steel ply cord spacing of 2.4mm. The upper and lower threshold voltage levels +V and −V of the afore-mentioned comparators 159 to 162 can be determined on the basis of the graph of FIG. 11. For example, where it is required to make a mark on all the tires which have an inter-cord spacing greater than 4mm, the upper and lower threshold voltage levels are set at +4.3V and −4.3V, respectively.

One cycle of the tire inspecting operation by the apparatus according to the invention proceeds in the following sequence. Referring to FIG. 1, the tires T to be subjected to the inspection are transferred onto the feeding conveyer 1 by a suitable conveying means (not shown) and caused to stand by on the conveyer 1 by the stopper mechanism 3. The stopper mechanism 3 releases one tire T in the most preceding position and allows the same to advance onto the conveyer 5. The tire T advanced onto the conveyer 5 is received by a centering mechanism (not shown) and held in a center position with the center of rotation of the tire T in registration with the center of rotation of the lower rim 30. Upon centering the tire T, the tire size detecting mechanism 66 is actuated to detect the outer diameter of the tire T, and transmits to the limit mechanism 139 a signal indicating the distance of travel required for the detector 105 to reach the side wall portion of the tire T to be inspected. The tire T is then released from the centering mechanism and raised together with the lower rim member 30 by the operation of the fluid-operated piston-cylinder 51 through the lever arm 47 and rim holders 46. In this instance, the tire T is securely retained on the lower rim 30 at its lower bead portion while being raised. As soon as the upper and lower rims 29 and 30 come into engagement with each other, the tire T is filled with compressed air which is fed from an air feed device (not shown) through the rubber hose 59, rotary joint 58, axial passage (not shown) in the shaft 44 and air blowing outlet (not shown) in the lower rim 30. The motor 33 is then started to rotate the shaft 31 and thus the tire T, through the reduction gear unit 34, sprocket wheels 38 and 40, and chain 41, while, the motor 131 is actuated to rotate the screw rod 130 through the reduction gear unit 132, thereby advancing the cord distribution detecting mechanism 97 by a specified distance. When the inspection of the cord distribution is completed after one full turn of the tire T, the air within the inspected tire T' is discharged and the piston-cylinder 51 is operated in a reverse direction to lower the lower rim 30 together with the inspected tire T', placing the latter on the roller conveyer 5. The tire T' is fed straight forward or dropped at the terminal end of the conveyor 6 by the operation of the piston-cylinder 7 depending on whether or not it bears a disqualifying mark as a result of the inspection.

By repeating the above-described cycle of operation, a number of tires T can be fed successively and automatically to check for any irregularities in the disposition of the steel ply cords St.

It will be appreciated from consideration of the foregoing description that, the apparatus according to the present invention can inspect dispositions of steel ply cords in pneumatic tires in a fully-automatic manner without depending upon the experience of the inspector and without resorting to a cost X-ray device, to provide safety-assured tires at a low cost.

What is claimed is:
1. An apparatus for automatically insecting the disposition of reinforcing steel ply cords in pneumatic tires, comprising in combination:
    a tire feeding mechanism for feeding tires one by one toward a predetermined position on said apparatus;
    a tire retaining mechanism having a rim member split into upper and lower halves for rotatably retaining a tire in an inspecting position;
    a rotational driving mechanism mechanically connected to said rim member for rotatingly driving the same;
    cord disposition detecting means including a carriage mounted on a machine frame so as to be movable toward and away from said inspecting position, and electric detectors mounted on said carriage to be movable toward and away from respective inspecting positions facing opposite side wall portions of said tire;

tire size detecting means comprising a cam shaft, an arm member securely mounted on said cam shaft and rotatingly movable toward a tread surface of a tire in said predetermined position, a number of cam plates securely mounted on said cam shaft and having angularly displaced cam surfaces relative to the axis of said cam shaft, and a number of limit switches securely mounted on a machine frame opposingly to said cam plates, said cam plates actuating said limit switches in a number corresponding to an angle of rotational movement of said arm member to produce a signal indicative of the size of said tire, and a limit mechanism for limiting the movement of said cord disposition detecting carriage, said limit mechanism comprising a plate member securely mounted on said carriage and having a number of consecutively stepped surfaces and a number of limit switches securely mounted on a machine frame opposingly to said consecutively stepped surfaces of said plate member so as to produce a step signal for stopping said cord disposition detecting carriage upon a specified distance movement thereof as determined by the tire size detecting means signal;
electric control circuit means connected to said electric detectors for producing a disqualifying signal upon detection of an irregularity in the disposition of the steel ply cords in said tire; and
classifying means for distinguishing a disqualified tire from qualified ones.

2. An apparatus as set forth in claim 1 comprising an upper vertical rotary shaft rotatably supported on a machine frame, an electric motor coupled to said upper shaft for rotatably driving the same, a lower vertical rotary shaft in axial alignment with said upper rotary shaft, said upper half of said rim member being secured to the lower end of the upper vertical rotary shaft, said lower half of said rim member being securely mounted at the upper end of said lower vertical rotary shaft, said lower vertical rotary shaft being movable up and down for moving said tire toward and away from said inspecting position and having an axially extending air passage connected to a compressed air source for blowing compressed air into said tire prior to the inspecting operation.

3. An apparatus as set forth in claim 1 comprising a screw rod rotatably mounted on a machine frame, and an electrical motor coupled to said rod to drive the same in rotation, said carriage of said cord disposition detecting mechanism being in threaded engagement with said screw rod for moving said carriage by a distance specified by the signal from said tire size detecting means.

4. An apparatus as set forth in claim 1, further comprising a marking member located in a position proximate detectors of said cord disposition detecting mechanism and connected to a fluid-operated actuator, and an electromagnetic valve means energized upon receipt of a disqualifying signal from said electric control circuit means for introducing operating fluid to said actuator for moving said marking member toward said tire to make a mark thereon.

5. An apparatus as set forth in claim 1, wherein said classifying means comprises a roller conveyer located swingably at the discharge end of said apparatus and a fluid-operated actuator connected to said conveyer to cause it to assume either a horizontal or slanted position for discharging qualified and disqualified tires in different directions.

6. An apparatus as set forth in claim 1, wherein said tire feeding mechanism comprises a roller conveyer and a stopper mechanism for advancing tires intermittently one by one upon completion of inspection of a preceding tire.

7. An apparatus as set forth in claim 6, wherein said stopper mechanism includes a pair of arms mounted swingably across a tire passage on said roller conveyer and a fluid-operated piston-cylinder coupled to said arms for intermittently opening said tire passage.

8. An apparatus as set forth in claim 1, wherein said detecting means of said cord disposition detecting mechanism includes primary and differential coils wound around an iron core and housed in a casing of a non-magnetic material and filled with a synthetic resin material; said primary coil being connected to an output terminal of an oscillator and said differential coil being connected to said control circuit through an amplifier.

9. An apparatus as set forth in claim 8, wherein said control circuit includes four parallel connected comparators, two of said comparators being calibrated to have a predetermined threshold voltage level in the positive phase and the other two of said comparators being calibrated to have a predetermined threshold voltage level in the negative phase, a first monostable multivibrator having an input terminal connected to an output terminal of one of said positively calibrated comparators, a second monostable multivibrator vibrator having an input terminal connected to an output terminal of one of said negatively calibrated comparators, a first AND circuit having an input terminal connected to output terminals of the other one of said positively calibrated comparators and said first monostable multivibrator, and a second AND circuit having an input terminal connected to output terminals of the other one of said negatively calibrated comparators and said second monostable multivibrator.

* * * * *